United States Patent
Ramalho et al.

(10) Patent No.: US 11,923,085 B2
(45) Date of Patent: Mar. 5, 2024

(54) SYSTEMS AND METHODS FOR USING ACOUSTIC COMMUNICATIONS FOR CONTACT TRACING WITHIN ADMINISTRATIVE BOUNDARIES

(71) Applicant: Michael A. Ramalho, Lakewood Ranch, FL (US)

(72) Inventors: Michael A Ramalho, Lakewood Ranch, FL (US); Gail W. Karaman, Lakewood Ranch, FL (US)

( * ) Notice: Subject to any disclaimer, the term of this patent is extended or adjusted under 35 U.S.C. 154(b) by 195 days.

(21) Appl. No.: 17/325,921

(22) Filed: May 20, 2021

(65) Prior Publication Data

US 2021/0375451 A1 Dec. 2, 2021

Related U.S. Application Data

(60) Provisional application No. 63/032,587, filed on May 30, 2020.

(51) Int. Cl.
*G16H 40/67* (2018.01)
*H04B 11/00* (2006.01)

(52) U.S. Cl.
CPC ............. *G16H 40/67* (2018.01); *H04B 11/00* (2013.01)

(58) Field of Classification Search
CPC ............................... H04B 11/00; G16H 40/67
See application file for complete search history.

(56) References Cited

U.S. PATENT DOCUMENTS

| | | | | |
|---|---|---|---|---|
| 3,779,237 A | * | 12/1973 | Goeltz | A61B 5/316 128/903 |
| 9,224,096 B2 | * | 12/2015 | Oppenheimer | G06N 3/08 |
| 10,169,985 B1 | * | 1/2019 | Rader | G08C 23/02 |
| 2004/0220487 A1 | * | 11/2004 | Vyshedskiy | A61B 7/04 600/528 |
| 2007/0197878 A1 | * | 8/2007 | Shklarski | A61B 5/0022 128/903 |

(Continued)

OTHER PUBLICATIONS

Payne, "NOVID is the Most Accurate App for Contact Tracing", Carnegie Mellon University News, https://www.cmu.edu/news/stories/archives/2020/june/novid-update.html, Jun. 30, 2020, retrieved on May 19, 2021, 3 pages.

*Primary Examiner* — Daniel L Murphy
*Assistant Examiner* — Amie M Ndure
(74) *Attorney, Agent, or Firm* — Mooney IP

(57) ABSTRACT

Systems, computer-implemented methods, and tangible non-transitory computer-readable media are provided for performing contact tracing using acoustic communications. For example, a computer-implemented method may include allocating an acoustic token for broadcasting via an audio communication channel, obtaining information associated with the acoustic token received from a first device of a first user based on the broadcasting of the acoustic token where the first user is associated with a disease, determining whether the information associated with the acoustic token from the first device relates to information associated with the acoustic token received from a second device of a second user, and providing information that indicates whether the second user was exposed to the disease based on whether the information associated with the acoustic token from the first device relates to the information associated with the acoustic token from the second device.

20 Claims, 9 Drawing Sheets

(56) References Cited

U.S. PATENT DOCUMENTS

| | | | | |
|---|---|---|---|---|
| 2007/0222599 A1* | 9/2007 | Coveley | ............. | G08B 13/2462 |
| | | | | 340/572.4 |
| 2008/0189360 A1* | 8/2008 | Kiley | ...................... | H04W 4/02 |
| | | | | 709/203 |
| 2010/0217100 A1* | 8/2010 | LeBoeuf | .............. | A61B 5/6826 |
| | | | | 600/382 |
| 2010/0315549 A1* | 12/2010 | Basso | ................ | H04N 21/4402 |
| | | | | 348/E7.003 |
| 2011/0301439 A1* | 12/2011 | Albert | .................... | G16H 40/63 |
| | | | | 600/509 |
| 2012/0092134 A1* | 4/2012 | Stern | .................... | G01S 13/765 |
| | | | | 340/10.1 |
| 2012/0229624 A1* | 9/2012 | Calman | ................ | H04W 4/029 |
| | | | | 382/218 |
| 2013/0044570 A1* | 2/2013 | Mkrtchyan | .............. | A63H 3/28 |
| | | | | 367/197 |
| 2013/0336497 A1* | 12/2013 | Duplan | ................ | H04B 11/00 |
| | | | | 381/77 |
| 2014/0104059 A1* | 4/2014 | Tran | ....................... | G16Z 99/00 |
| | | | | 340/539.12 |
| 2014/0185862 A1* | 7/2014 | Kamath | ............. | G06Q 20/3829 |
| | | | | 382/100 |
| 2015/0244472 A1* | 8/2015 | Poppe | ................... | H04B 11/00 |
| | | | | 367/135 |
| 2016/0104190 A1* | 4/2016 | Webster | .................... | G06F 9/44 |
| | | | | 705/14.4 |
| 2016/0140839 A1* | 5/2016 | Hsieh | ....................... | H03J 9/04 |
| | | | | 367/199 |
| 2016/0241645 A1* | 8/2016 | Sabbaghian | ....... | G06Q 30/0265 |
| 2016/0260161 A1* | 9/2016 | Atchley | ................. | A47F 10/04 |

* cited by examiner

SYSTEMS AND METHODS FOR USING ACOUSTIC COMMUNICATIONS FOR CONTACT TRACING WITHIN ADMINISTRATIVE BOUNDARIES

CROSS-REFERENCE TO RELATED APPLICATION

The present application claims the benefit of U.S. Provisional Patent Application No. 63/032,587, filed May 30, 2020, and entitled "System and Method Using Acoustic Communications for Contact Tracing within Administrative Boundaries," which is hereby incorporated by reference herein in its entirety.

FIELD

The present disclosure generally relates to the use of acoustic communication technology in computer systems. More particularly, the present disclosure relates to the use of acoustic communication technology in association with various types of computer systems and computing devices for the purpose of assessing epidemiologically significant exposure to various forms of disease.

BACKGROUND

Contact tracing generally refers to the process of identifying individuals who may have come into contact with a person infected by a communicable disease. By tracing the contacts of infected individuals, testing such contacts for infection, isolating and treating infected contacts, and tracing the contacts of exposed and infected individuals, organizations can reduce the spread of infectious disease. In particular, contact tracing becomes especially important during the rapid spread of disease associated with epidemics and pandemics. As such, a need exists for providing improved ways of performing contact tracing with greater efficiency, accuracy, and coverage.

SUMMARY

Aspects and advantages of embodiments of the present disclosure will be set forth in part in the following description, or can be learned from the description, or can be learned through practice of the embodiments.

One example aspect of the present disclosure is directed to a computer system that performs contact tracing using acoustic communications. For example, the computer system may include one or more processors and one or more non-transitory computer-readable media storing instructions that, when executed by the one or more processors, cause the computer system to perform operations. For example, such operations may include allocating an acoustic token to an emitting device for broadcasting via an audio communication channel, obtaining information associated with the acoustic token from a first user device of a first user where the information associated with the acoustic token from the first user device is based on the broadcasting of the acoustic token from the emitting device to the first user device and where the first user of the first user device is associated with a disease, determining whether the information associated with the acoustic token from the first user device of the first user relates to information associated with the acoustic token from a second user device of a second user, and outputting, based on the determining, information indicating whether the second user had exposure to the disease.

Another example aspect of the present disclosure is directed to a computer-implemented method for performing contact tracing based on acoustic communications. For example, a computer-implemented method performed by one or more processors may include allocating an acoustic token to an emitting device for broadcasting via an audio communication channel, obtaining information associated with the acoustic token from a first user device of a first user where the information associated with the acoustic token from the first user device is based on the broadcasting of the acoustic token from the emitting device to the first user device and where the first user of the first user device is associated with a disease, determining whether the information associated with the acoustic token from the first user device of the first user relates to information associated with the acoustic token from a second user device of a second user, and outputting, based on the determining, information indicating whether the second user had exposure to the disease.

A further example aspect of the present disclosure is directed to one or more tangible non-transitory computer-readable media storing computer-readable instructions that, when executed by one or more processors, cause the one or more processors of a computing device to perform operations. For example, the operations may include allocating a unique acoustic token to an emitting device for broadcasting via an audio communication channel, obtaining information associated with the unique acoustic token from a first user device of a first user where the information associated with the unique acoustic token from the first user device is based on the broadcasting of the unique acoustic token from the emitting device to the first user device and where the first user of the first user device is associated with a disease, determining whether the information associated with the unique acoustic token from the first user device of the first user relates to information associated with the unique acoustic token from a second user device of a second user, and outputting, based on the determining, information indicating whether the second user had exposure or possible exposure to the disease.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to those skilled in the art is set forth in the specification, which makes reference to the appended figures, in which.

DETAILED DESCRIPTION

Figure 1:
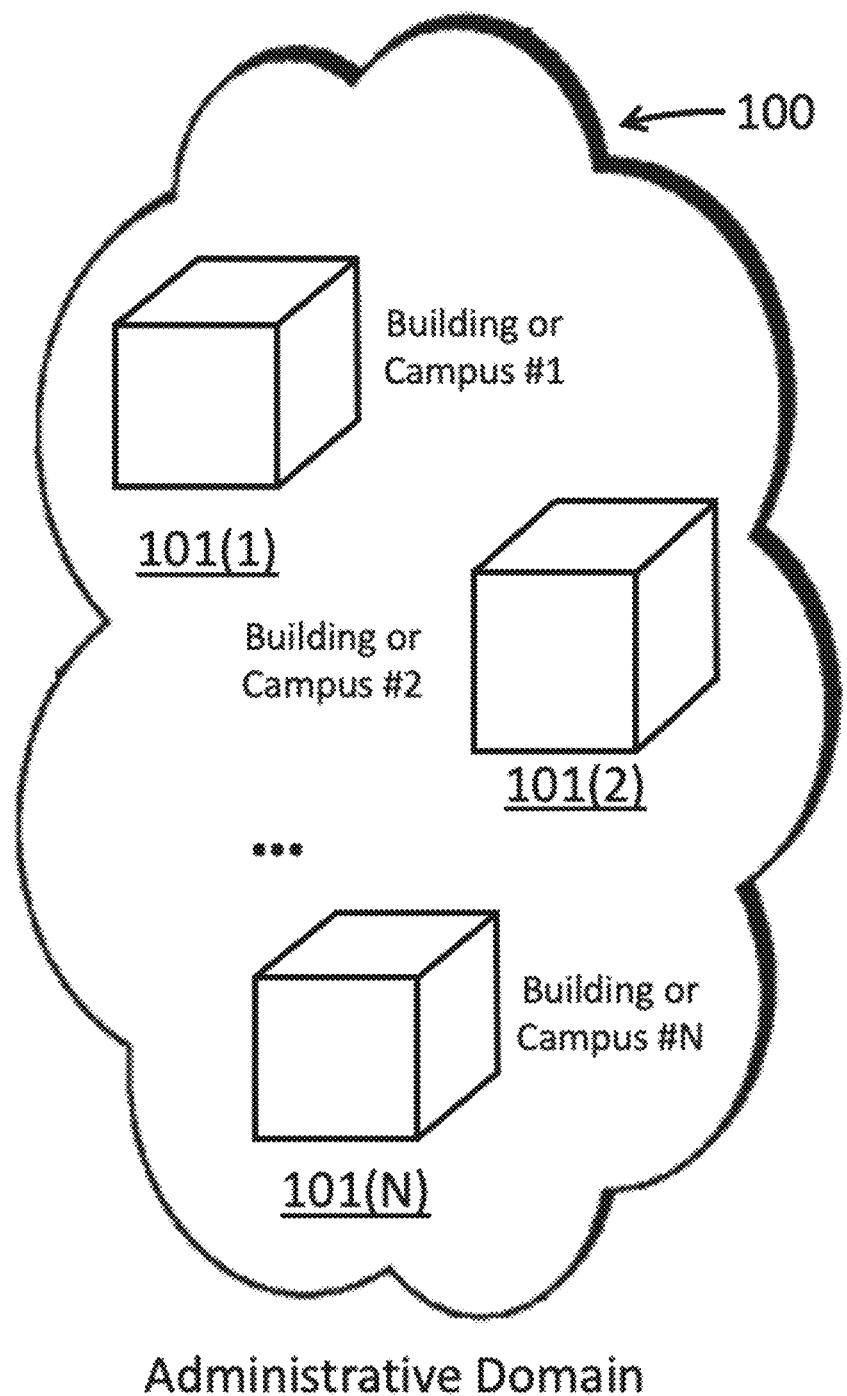
FIG. 1 is an illustration depicting an example of an administrative domain environment, according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a further embodiment. Thus, it is intended that aspects of the present disclosure cover such modifications and variations.

During periods of an endemic, epidemic, pandemic and/or any other spread of disease, there is a desire for employers (both public and private), service providers, and other entities to provide notice to employees, contractors, customers, and/or other parties that may have been exposed to a diseased person (e.g., a person infected with a communicable disease, a person believed to be infected with a communicable disease, etc.) for an epidemiologically significant amount of time. A preferred embodiment of this disclosure uses acoustic communications (e.g., initially developed for different end goals) that may be leveraged via system design enhancements and/or other modifications to provide such notification.

As an illustrative example, ultrasonic information may be transmitted from a variety of unified communications endpoints, such as videoconferencing systems, video phones, and the like, so that users may pair (e.g., associate) their endpoints (hereinafter "user endpoints") to those devices (hereinafter "system endpoints"). In an example, various types of systems may emit "information tokens" (e.g., acoustic tokens) from the system endpoints which, when received and decoded by user endpoints, are transmitted back to the videoconferencing system provider infrastructure in order to make an association between the system endpoint and the user's endpoint. For example, such various types of systems can be deployed in enterprise locations (e.g., businesses, governments, etc.) for use by employees.

In an example, such user endpoint devices (e.g., Mac® computers, PCs, and iOS® or Android® phones) may have software to decode the information tokens sent by the system endpoints where the user (e.g., an employee) has agreed to appropriate use of receiving and sending such token information in either their terms of employment (e.g., via an agreement) or by another appropriate opt-in, privacy policy, or terms-of-use provision.

In the normal operation of systems such as these, the information tokens e.g., acoustic tokens) are frequently refreshed so that there is no long-term association between a specific token and a specific system endpoint. A valid token at one instant will become stale (e.g., have no useful value for pairing) a short time after such refresh, although a given token may be reused after an appropriate period of non-use. For this reason, these systems generally have little or no need to keep a long-term history of when a particular token was emitted from a given system endpoint in a given room at a given time. Examples of the present disclosure change this paradigm to provide contact tracing within administrative boundaries, while still leveraging the concept of such tokens (e.g., acoustic tokens) being emitted from those system endpoints at a certain time and at a certain place. Examples of the present disclosure also describe an "information token allocation and delivery service," which provides unique tokens to system endpoints via standard networking services in association with other operations.

System endpoints such as these can be placed in specific acoustic volumes (e.g., a conference room, huddle room, private office, etc.) where sound-based communication techniques may be used, for example, instead of other potential pairing technologies (e.g., Bluetooth®). This is because sound-based communications can be made local to the desired acoustic volume. As such, it is important for the purposes of this disclosure to decouple physical-distance proximity from acoustic proximity. For example, two people on different sides of a common wall may be close to each other in a radio frequency (RF) sense but "not in proximity" to each other in an acoustic or epidemiologically significant sense. As such, two apartments with adjacent bedrooms can have cellphones that can communicate via Bluetooth® technology on end tables separated by as little as one meter from one another. However, the occupants of the different rooms pose little disease exposure risk due to the physical separation of the apartment-dividing wall. Similarly, this applies to office rooms in enterprise settings, many hospital room settings, and/or many other types of physical settings. Nonetheless, RF solutions (e.g., such as Bluetooth® beacons) may be used, for example, in conjunction or combination with examples of the present disclosure.

In the present disclosure, an "acoustic volume" is not limited to the typical sense of a space e.g., the product of the length, width, and height of a rectangular room). Instead, an "acoustic volume" generally may refer to any space within which acoustic information transmission has been designed to take place or otherwise takes place from a specific system device to a user device that is nearby (e.g., to any user device that receives acoustic information transmitted by another device). Such user devices can be said to be in "acoustic proximity" to the system device. Also, there may be multiple "acoustic volumes" within a larger physical room's volume (or in any space), which may overlap with one another. In addition, "acoustic volumes" are not limited to enclosed, semi-enclosed, or indoor spaces and generally may include any type of open space, outdoor space, hybrid indoor-outdoor space, and/or any other type of space where transmission of acoustic information can occur from one device to another device. Related examples are provided in the embodiments described throughout the present disclosure.

One important objective of the present disclosure is to make an association between persons (or, more precisely, their user endpoints) that have been in epidemiologically significant proximity in a specific acoustic volume for an epidemiologically significant exposure time by use of the correlation of the information tokens received by their user devices. For example, such correlation may occur after one (or more) of the persons is known to be diseased. Also, such correlation may take place in a back-end setting where data stored in the relevant databases are used to make the correlation. In a preferred embodiment, both the information tokens emitted by a system endpoint and the information tokens received by the user endpoint are anonymized before being stored in a database. In this way, any party (including third parties) can make such an association from the token data in those databases in a privacy-conserving manner. In some examples, the entity making an association between specific user endpoints and specific system emitters is the local administrative domain (or a larger federation of such domains) that already has obtained user consent to make such a correlation. In some examples, tokens may be kept in the database(s) for a minimum of the worst-case time between exposure and symptom onset (or positive disease diagnosis for symptomatic cases and/or asymptomatic cases), but for privacy reasons may not be kept for significantly longer.

The videoconferencing system example mentioned above is non-limiting and provided for illustrative purposes only. For example, the form of acoustic communication may be spread-spectrum or non-spread-spectrum based, may employ modulation of any form (e.g., AM, QAM, PSK, etc.) or be baseband, or occupy bearable and/or non-bearable (e.g., ultrasound) frequencies. Additionally, examples of the present disclosure may include the use of any other system and/or computing devices that are capable of both sound generation and network communication (e.g., IP phones). Many types of consumer devices include both audio output capabilities in excess of those required as well as the required networking capabilities (e.g., Raspberry Pi® with audio output, smart home computer devices, smart speaker devices and hardware, virtual assistant devices and hardware, wearable devices, etc.). These devices as well as other non-consumer devices (e.g., IoT devices, access-control hardware, smart building computing devices, industrial devices and/or other machines with computing capabilities, etc.) or custom devices that can both emit acoustic tokens and communicate information to back-end infrastructure and databases can also be used as system devices.

Examples of the present disclosure may include the use of user devices other than the Mac® computers, PCs, and iOS® or Android® phones mentioned above as long as such devices have the required software, audio recording, and networking capabilities. Additionally, similar to the unified communications example above, the users should have agreed to appropriate use of receiving such communications on their devices.

Examples of the present disclosure may include the use of a specially designed system or any type of adjunct, improvement, and/or customization to an existing system (e.g., an access control system) that can be made to operate in a similar manner (e.g., by emitting information tokens from system endpoints to user endpoints). In various examples, such a system may include an information token allocation and delivery service which allocates unique system tokens to system devices in known acoustic volumes with a send duration (or change frequency) and may include a token reuse strategy consistent with examples of the present disclosure (e.g., for assessing epidemiologically significant exposure to diseased individuals). In an example, such a system or service may include one or more operations that differ from the unified communications example above. For example, the token duration strategy, the database retention strategy and/or the privacy-preserving requirements for the tokens stored in databases may be outside the control of the administrative domain boundary. Additionally, the database(s) storing the tokens (e.g., either emitted tokens, received tokens, or both emitted and received tokens) may or may not reside in the same infrastructure as the information token allocation and delivery service.

Examples of the present disclosure also may include the use of token/information exchange in the reverse direction (user device to system device) as well as bidirectional information exchanges between different devices. Accordingly, such embodiments are explicitly included in this disclosure.

A preferred embodiment of this disclosure uses the acoustic communications developed for different purposes (e.g., for unified communications and/or for any other purpose) to be leveraged via system design enhancements and modifications to provide notification for the purpose of assessing epidemiologically significant exposure to diseased individuals within an administrative domain. One such example is the unified communications example mentioned above where acoustic communications described herein can be used to make an association between a system endpoint and a user's endpoint. Similarly, in an access control example, acoustic communications described herein can be used to associate an access control endpoint (e.g., a badge reader-like device) and a user's endpoint (e.g., such as a smartphone).

As many such systems and associated computing devices can be enhanced and modified for the purposes of this disclosure, the example embodiments described herein will focus on the elements for providing acoustic communications for contact tracing within administrative boundaries. Such elements may include, but are not limited to, the system endpoints (e.g., computing devices or any other types of machines or devices) that emit the information tokens acoustically (referred to hereinafter as system endpoints, token emitters, or just emitters), one or more user computing devices such as smartphones, laptops, wearable devices, and/or any other type of computing devices that may receive and decode the information token sent acoustically (hereinafter referred to as user endpoints), an infrastructure computing system that has allocated tokens for durations and periods of non-overlapping use in accordance with examples of the present disclosure, one or more databases or other types of data storage for maintaining the sent and received information tokens, and a token correlation service that performs token correlation processing, The systems, methods, and computer program products described herein provide a number of technical effects and benefits. As one example, the embodiments described in the present disclosure provide various systems and methods for utilizing acoustic communications involving multiple computing devices to perform contact tracing more accurately and more efficiently within an administrative domain (or federation of administrative domains), than would otherwise be wasted by performing conventional or manual processes. In addition, various embodiments described in the present disclosure enable such contact tracing to be performed while preserving user privacy including privacy of user movement occurring in one or more administrative domains.

With reference to the Figures, example embodiments of the present disclosure will be discussed in further detail.

FIG. 1 depicts the concept of an Administrative Domain (AD) for the purposes of this disclosure. As an example, the AD 100 could be that of a private company that has employees, contractors, vendors, and the like that have the need to visit one or more of the buildings, offices, and/or campuses of the company. Another example might be a hospital health system with various branches. In preferred embodiments, the contact tracing described herein is local to AD 100. As such, the appropriate user opt-in, privacy, and/or terms-of-use issues are local to the AD (a federation of ADs is discussed later). AD 100 includes individual buildings or campuses that are labeled as 101(1) through 101(N).

Figure 2:
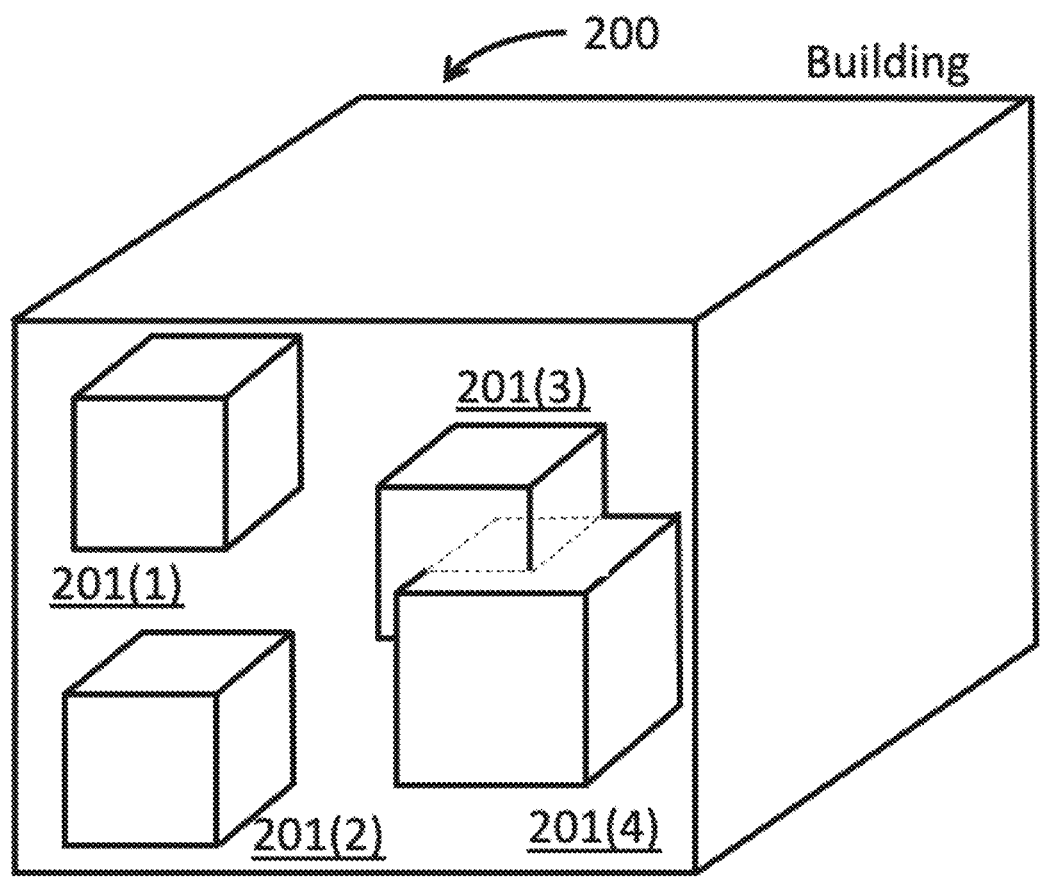
FIG. 2 is an illustration of an example of acoustic volumes, according to example embodiments of the present disclosure.
Figure 3:
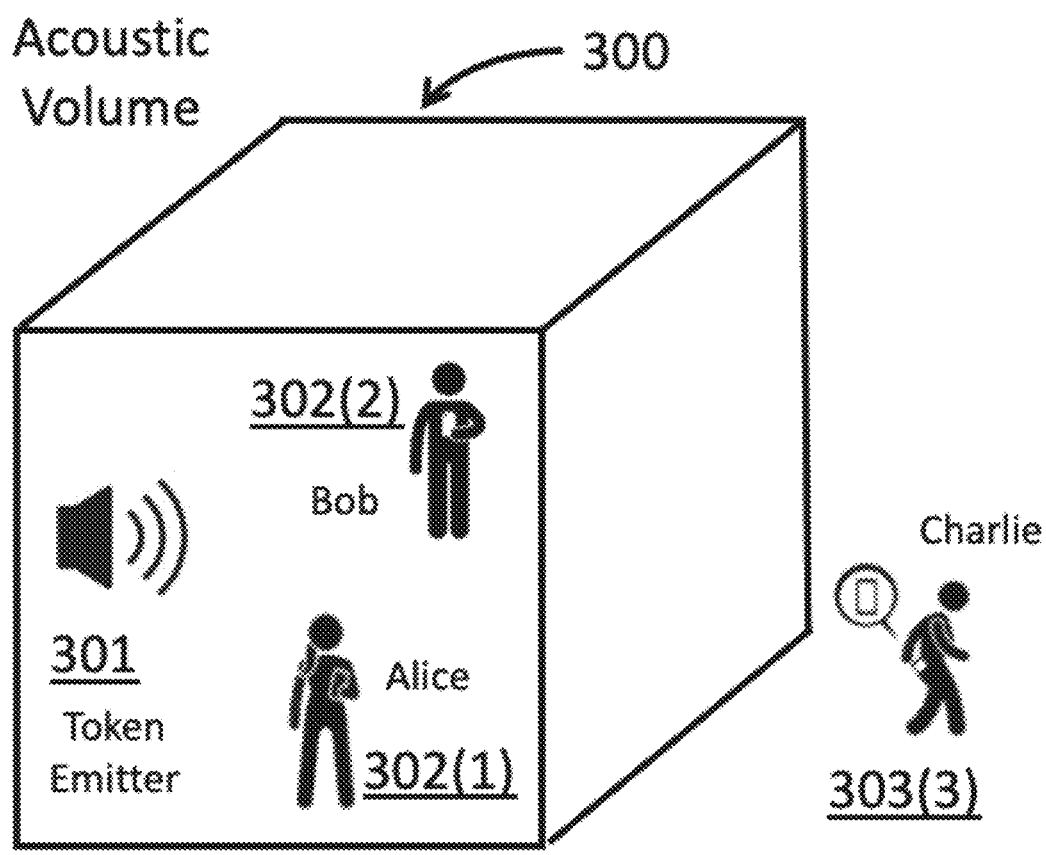
FIG. 3 is an illustration depicting an example environment with two users and an acoustic token-emitting system device within an acoustic volume and one user outside the acoustic volume, according to example embodiments of the present disclosure.

FIG. 2 is an illustration of an example of acoustic volumes, according to example embodiments of the present disclosure. In FIG. 2, a singular Building 200 includes one or more acoustic volumes ("AVs") labeled AV 201(1) through AV 201(4). As an example, one of these AVs might be a conference room or an individual's private office. These AVs are meant to show a space where acoustic communication of information tokens is local in the sense that user endpoints can decode the information tokens while within the AV. Also depicted are AVs where the volumes overlap, such as AV 201(3) and AV 201(4). This can occur because a user endpoint may be able to receive tokens being emitted from more than one AV. For example, multiple system endpoint emitters may also be placed in open floorplan arrangements in which the AVs may overlap. In particular, user endpoints in a given AV that belong to different users may be close enough and have exposure long enough for the purposes of contact tracing described herein, FIG. 3 depicts how users (more precisely their user devices) are associated with a given AV by decoding information tokens local to an AV. FIG. 3 shows an example of an AV 300 where a Token Emitter 301 (e.g., of a system endpoint) is emitting information tokens. Two user endpoints (e.g., User Endpoint 302(1) and User Endpoint 302 (2), belonging to Alice and Bob respectively) are in the same AV as Token Emitter 301, whereas the User Endpoint 303(3) (belonging to Charlie) is not in AV 300. The system will make the association that Alice's and Bob's user endpoints are in AV 300 and will determine the time period of overlap where they (or their endpoints) both were in AV 300.

Figure 4A:
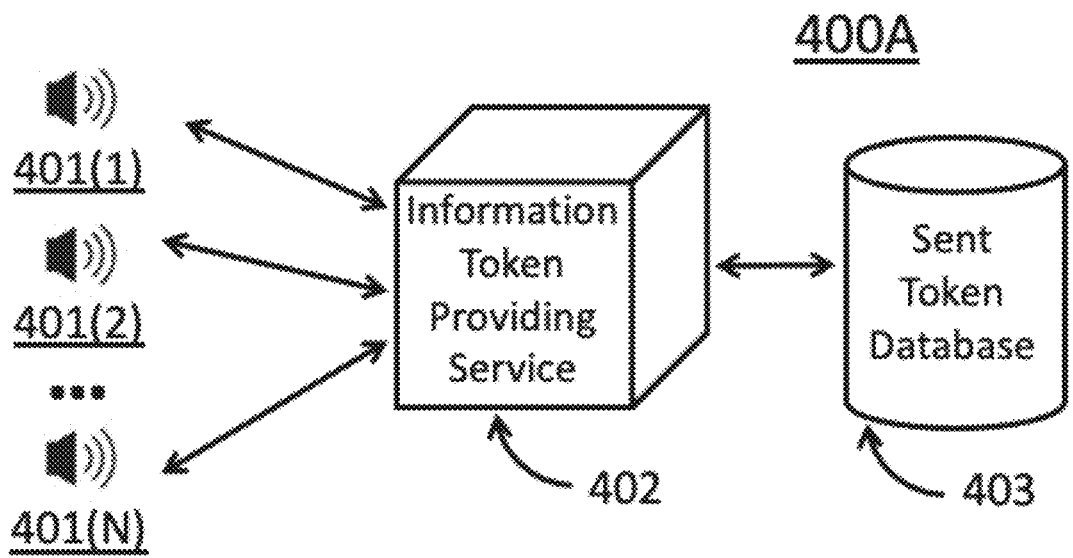
FIG. 4A is an illustration depicting an example where an acoustic token-emitting system device sends token and/or token timing information to a database, according to example embodiments of the present disclosure.
Figure 4B:
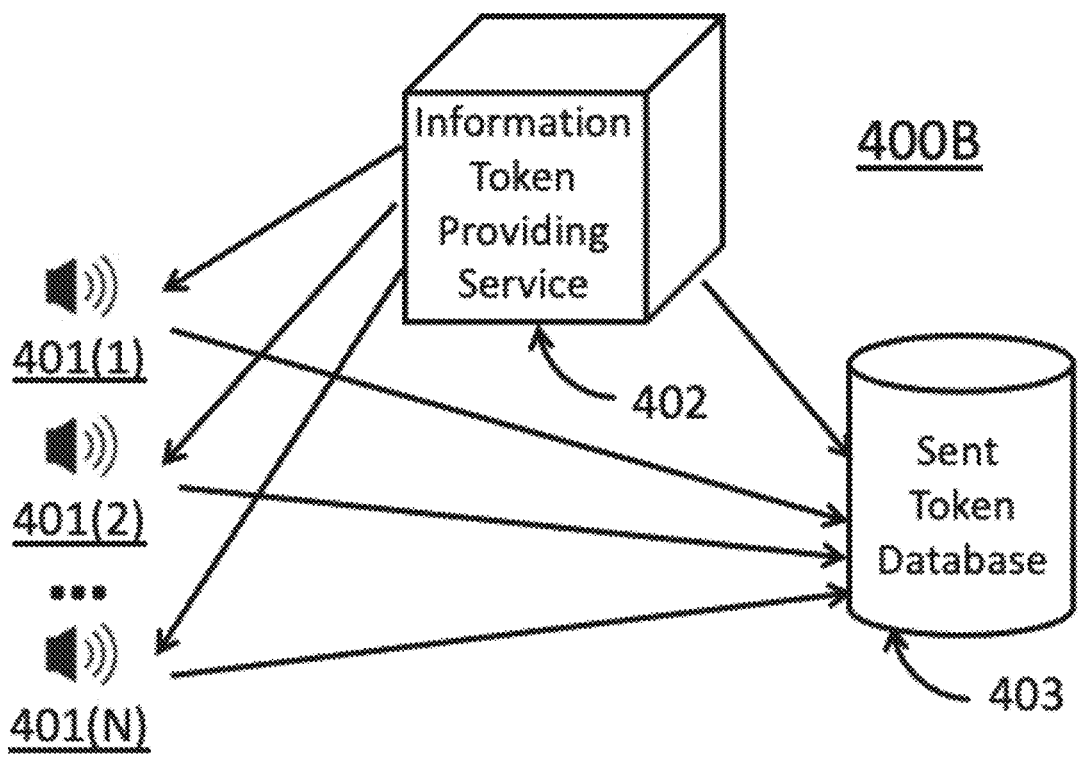
FIG. 4B is an illustration depicting an example where an acoustic token-emitting system device and/or system endpoints may send token and/or token timing information to a database, according to example embodiments of the present disclosure.

FIG. 4A and FIG. 4B each depicts an embodiment of how the Information Token Allocation and Delivery Service, the system endpoint Token Emitters, and the Sent Token Database can interact. In FIG. 4A, FIG. 4B, and subsequent figures and descriptions, the Information Token Allocation and Delivery Service is labeled and referred to more compactly as the "Information Token Providing Service." In FIG. 4A, System 400A depicts the Information Token Providing Service 402 interacting with system endpoint Token Emitters 401(1) through 401(N) and instructing each of them to send a specific information token for a particular duration at a predetermined time. In System 400A, the Information Token Providing Service also sends this information directly to the Sent Token Database 403.

In FIG. 4B. System 400B depicts an embodiment where the individual system endpoint Token Emitters 401(1) through 401(N) send the token information and the duration and time information directly to the Sent Token Database 403. Persons skilled in the art will recognize that other operations can be employed where the data (e.g., information associated with sent tokens) can go elsewhere through differing system elements in different embodiments, and thus be relayed through elements that are not shown. Additionally, the Information Token Providing Service 402 may be a functional entity (e.g., an entirely functional entity) whereby the sent tokens are defined by, a pre-programmed algorithm and may, thus, negate the need for a Sent Token Database 403. Also, not shown for simplicity, non-acoustic information may be carried over wired and/or wireless networks between the elements.

Figure 5A:
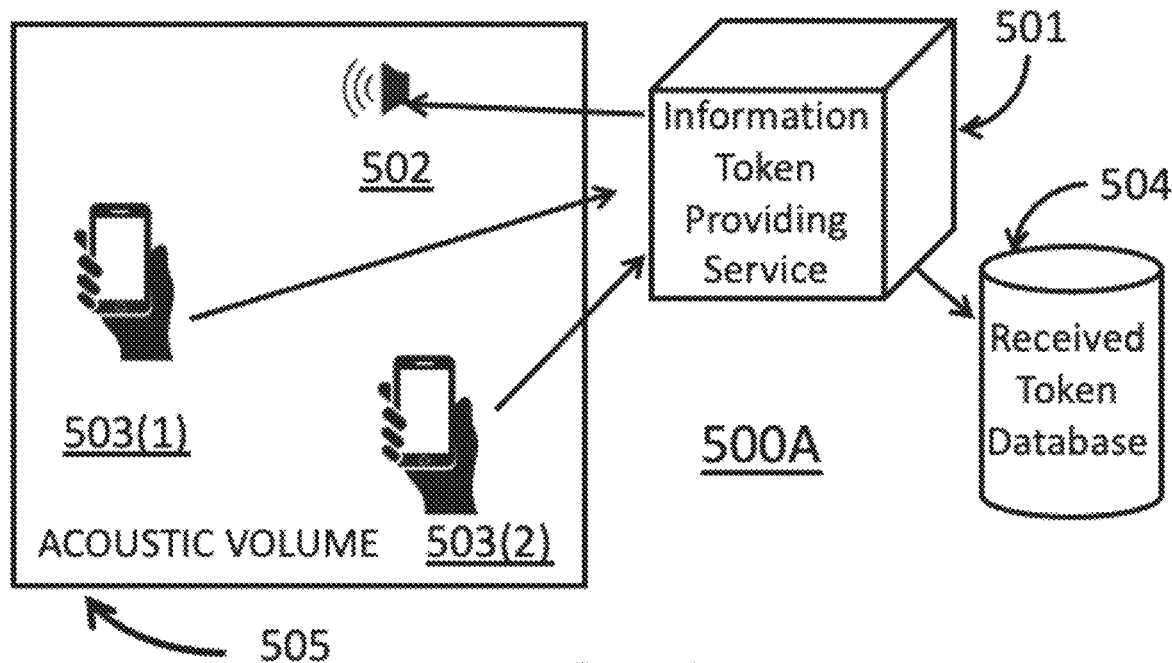
FIG. 5A is an illustration depicting an example of providing token and/or token timing information received from user devices to a database, according to example embodiments of the present disclosure.
Figure 5B:
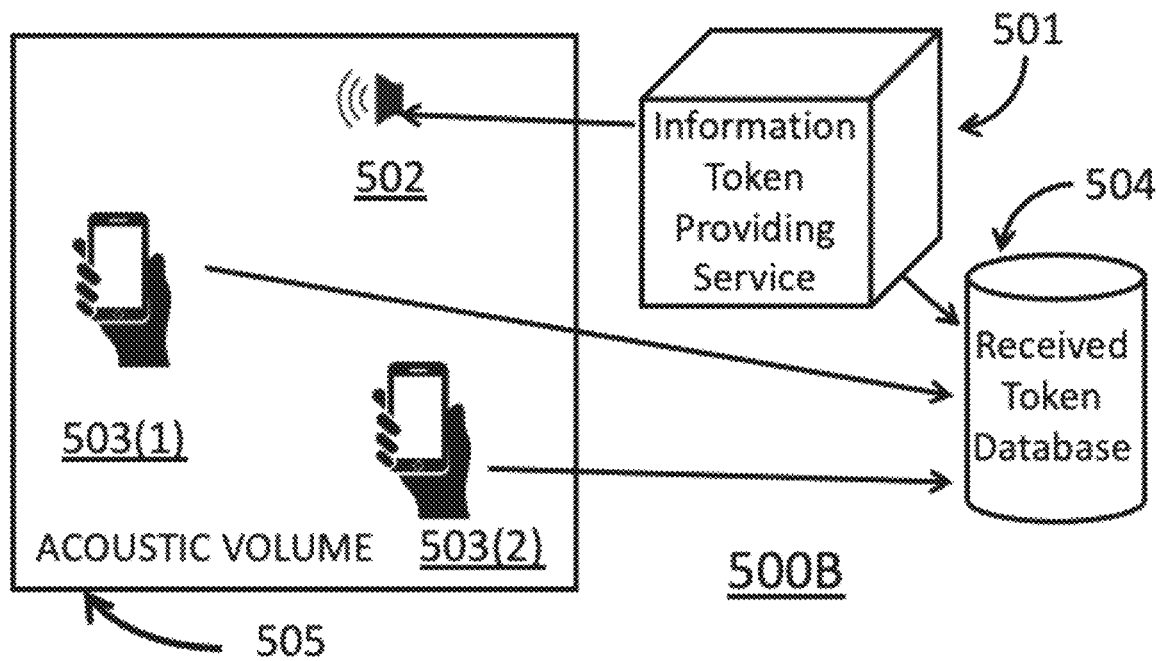
FIG. 5B is an illustration depicting an example of providing token and/or token timing information associated with a user device to a database, according to example embodiments of the present disclosure.

FIG. 5A and FIG. 5B each depicts an embodiment of how the Information Token Providing Service, User Endpoints, and the Received Token Database can interact. In FIG. 5A, System 500A depicts the Information Token Providing Service 501 interacting with the system endpoint Token Emitter 502 and instructing it to send a specific information token for a particular duration at a predetermined time in a specific AV 505. In System 500A, the information Token Providing Service 501 obtains received information token data from user endpoints (here User Endpoint 503(1) and User Endpoint 503(2)) and forwards that information to the Received Token Database 504. When examples of the present disclosure are used in association with modification of an existing system (e.g., one or more unified communications systems, access control systems, and/or any other types of systems), the example topology of System 500A can be employed as the Information Token Providing Service 501 and can be incorporated inside of a larger system design (e.g., inside of another system element and/or other computing device that is not shown).

In FIG. 5B, System 500B includes an alternative embodiment where the User Endpoints 503(1) and 503(2) forward the received information token and/or data associated with the received information token unique identifier, duration and/or time information, anonymized user device information, etc.) to the Received Token Database 504. Persons skilled in the art will recognize that other operations can be employed where the data (e.g., information associated with the received tokens) can go elsewhere through differing system elements in different embodiments, and thus be relayed through elements that are not shown. Also not shown for simplicity, non-acoustic information may be carried over wired and/or wireless networks between the elements.

In some embodiments (e.g., such as embodiments pertaining to FIG. 5A and FIG. 5B), the User Endpoints can decode an acoustic signal to produce the received information token data. However, persons skilled in the art will recognize that raw received audio (e.g., an acoustic token) may be provided by the User Endpoints to other system elements and/or devices (not depicted here), which then decode such audio to obtain received information token data that can be forwarded/relayed to the Received Token Database 504. Persons skilled in the art also will recognize that the Received Token Database 504 of FIG. 5A and FIG. 5B, and the Sent Token Database 403 of FIGS. 4A and 4B may be realized in the same physical hardware.

Figure 6:
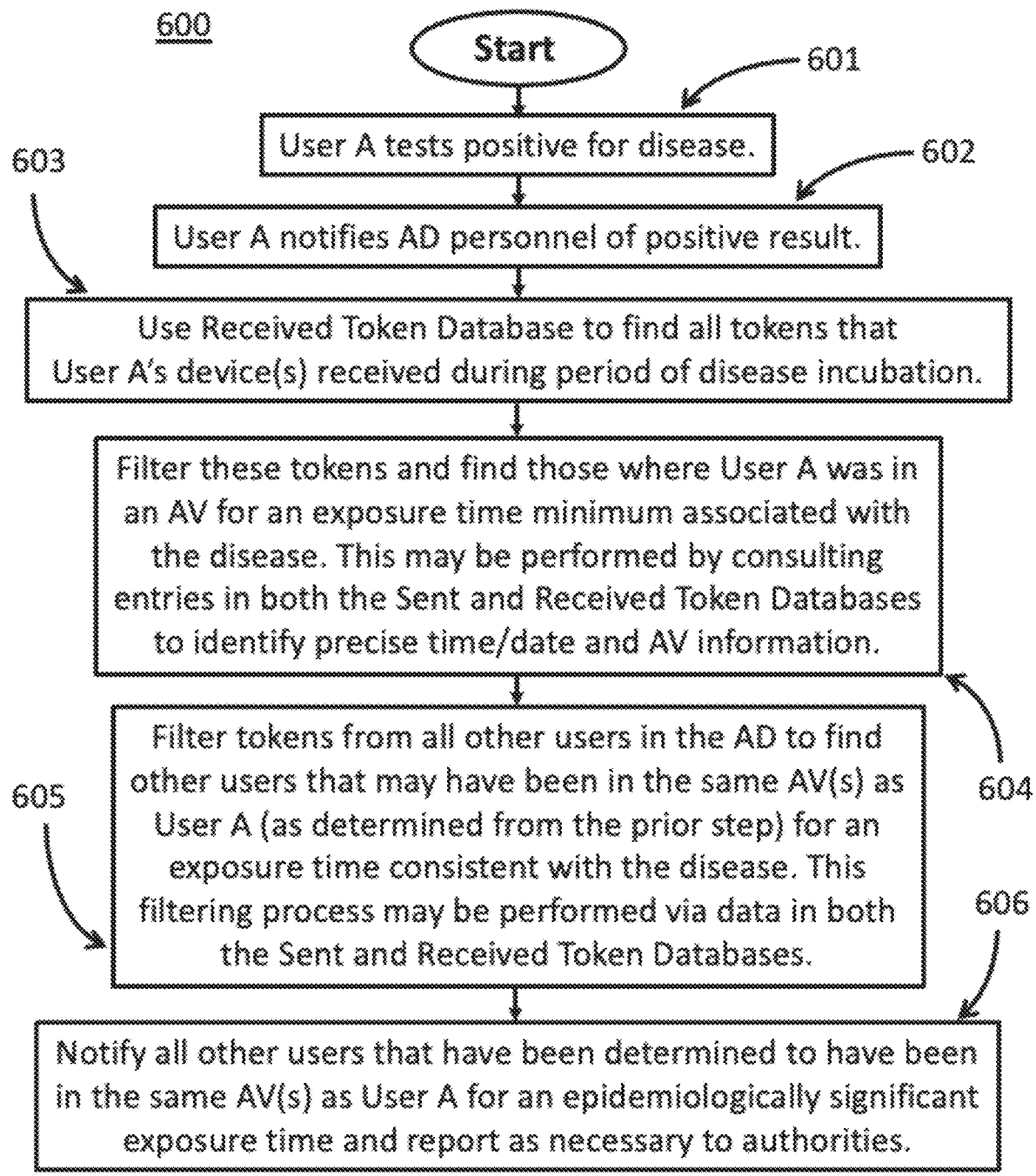
FIG. 6 is a flow diagram of an example method for performing contact tracing using information associated with acoustic communications, according to example embodiments of the present disclosure.

FIG. 6 is a flow diagram of an example method 600 for performing contact tracing using information associated with acoustic communications, according to example embodiments of the present disclosure. One or more portions of the example method 600 can be executed and/or implemented on one or more computing devices or computing systems. In addition, one or more portions of the example method 600 can be executed or implemented as an algorithm on the hardware devices or systems disclosed herein. FIG. 6 depicts steps performed in a particular order for purposes of illustration and discussion. As such, those skilled in the art, using the disclosures provided herein, will understand that various steps of any of the methods disclosed herein can be adapted, modified, rearranged, omitted, and/or expanded without deviating from the scope of the present disclosure.

At Step 601, "User A" learns that they have tested positive for a disease within the scope of this disclosure. At Step 602 "User A" notifies the AD personnel or the contact tracing system of their positive test result, for example, by calling, by messaging, by email, or via direct interaction with a contact tracing application user interface provided via a computing device (e.g., provided via one of "User A's" User Devices).

In an embodiment, a contact tracing procedure comprising one or more of Step 603, Step 604, Step 605, and/or Step 606 can occur. In an example, at Step 603 token information associated with one or more AVs (e.g., AV 201(1)-AV 201(4)) and "User A's" user endpoint(s) are found from Received Token Database 504. At Step 604 this token information is further filtered to provide the subset of tokens which meet the time/date and exposure time criterion appropriate for the disease. In an example, Step 604 may involve searching and filtering through both Sent Token Database 403 and Received Token Database 504, as the time duration of the sent token may only be kept in the Sent Token Database 403. In Step 605, received tokens from other users in the AD (e.g., AD 100) are searched to find one or more other users (e.g., all other users) that may have been in contact with "User A" for an exposure time consistent with the disease. In some examples, it can be assumed that if both users were in the same AV for the requisite time, then such contact may have occurred. As an example, Step 605 (e.g., similar to Step 603 and Step 604), may involve searching and filtering through both Sent Token Database 403 data and Received Token Database 504 data. At Step 606, the individual users that may have been exposed to "User A" for an epidemiologically significant exposure time are notified and any required reports are generated for appropriate authorities (e.g., the Centers for Disease Control and Prevention "CDC" in the United States and/or any other appropriate organizations).

Persons skilled in the art will appreciate that some of the aforementioned steps can occur in parallel and/or in a different order to achieve the same result. Also, persons skilled in the art will recognize that the processing involved with Steps 603, Steps 604, and Steps 605 may be executed with any combination of existing system components (e.g., Information Token Providing Service 402, Sent Token Database 403, Received Token Database 504) and/or with any other computer system components that are not depicted. Further, persons skilled in the art will appreciate that information sent to the Sent Token Database 403 and the Received Token Database 504 may be anonymized such that the only entity able to make a hard association between a specific user and a specific AV is the AD for that data. Thus, as an example, if such an anonymization is employed, then a third-party entity/service may, for example, perform Step 603, Step 604, and Step 605 based on the anonymized data labels (e.g., without revealing, knowing, or using identifying information of specific users, specific user devices, specific system devices, and/or AVs).

Figure 7A:
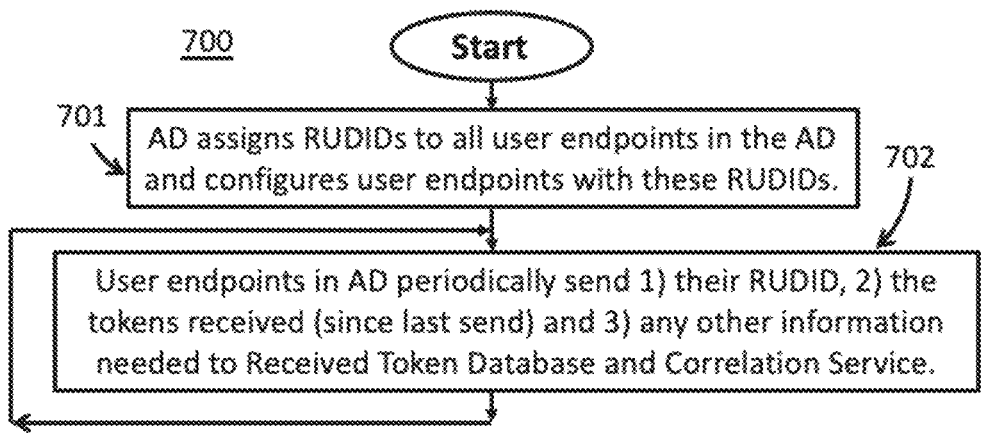
FIG. 7A is allow diagram of an example method for performing operations that support contact tracing based on acoustic communications while protecting the privacy of user movements within the administrative domain, according to example embodiments of the present disclosure.
Figure 7B:
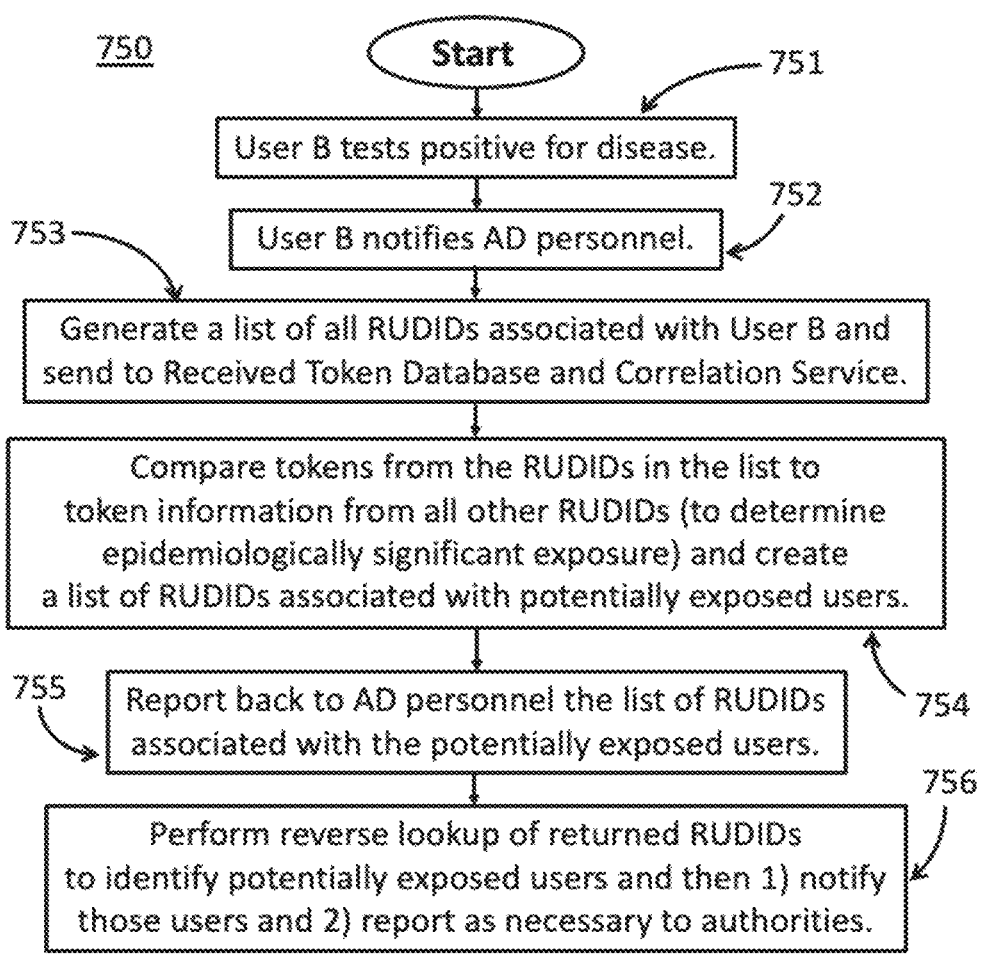
FIG. 7B is a flow diagram of an example method for performing operations that support contact tracing based on acoustic communications while protecting the privacy of user movements within the administrative domain, according to example embodiments of the present disclosure.

FIG. 7A and FIG. 7B are flow diagrams with respective example methods for performing operations that support contact tracing based on acoustic communications while protecting the privacy of user movements within the AD. For example, operations associated with such examples generally can protect the privacy of user movements within the AD. As such, AD personnel can identify potential exposure(s) without specific access to or knowledge of information indicating where potential exposure(s) occurred (e.g., one or more specific AVs where potential exposure(s) occurred). Instead, AD personnel may be made aware that a diseased individual had exposure(s) to one or more other individuals in one or more AVs within the AD. As an example, received tokens generally may not be identified as being associated with a specific AV before and/or when identifying potentially exposed individuals (e.g., as included in portions of Step 604 and Step 605 of FIG. 6). As such, a party can perform contact tracing, for example, based on knowing that the potentially exposed individual's user endpoints received the same tokens (e.g., at the same time, at approximately the same time, within a particular period of time, etc.) as the diseased individual's user endpoints for an epidemiologically significant exposure time. In an embodiment, information in the Sent Token Database 403 may not be used in performing contact tracing, because the associated processing can be performed via correlating the received tokens of the diseased person's user endpoints to those of the potentially exposed individual's user endpoints using data stored in the Received Token Database 504.

In an embodiment, to attain the goal of AD personnel being unaware e.g., not knowing) where the exposure(s) occurred, it may be advantageous for a received token database (e.g., Received Token Database 504) to be administered by a trusted third party and for the trusted third party to provide one or more operations associated with token correlation. In various examples, such combined operations generally may be referred to as a "trusted received token database and correlation service." Additionally, if for privacy purposes the identity of the individual user should remain undisclosed to the third party, then the individual user device identification in database records can be anonymized. Further, if the tokens sent by one or more system emitters are not unique across an incubation time period of the disease (e.g., they may only be unique for a lesser time in an existing system), then it may be advantageous that all token records sent to the Received Token Database 504 have a timestamp as to when they were received. Example method 700 and example method 750, described below, generally may be based on the examples noted above.

FIG. 7A is a flow diagram of an example method 700 for performing operations that support contact tracing based on acoustic communications while protecting user privacy (e.g., protecting privacy of users, protecting personally identifiable information of users, protecting privacy of user movement within an administrative domain, etc.). One or more portions of the example method 700 can be executed and/or implemented on one or more computing devices or computing systems. In addition, one or more portions of the example method 700 can be executed or implemented as an algorithm on the hardware devices or systems disclosed herein. FIG. 7A depicts steps performed in a particular order for purposes of illustration and discussion. As such, those skilled in the art, using the disclosures provided herein, will understand that various steps of any of the methods disclosed herein can be adapted, modified, rearranged, omitted, and/or expanded without deviating from the scope of the present disclosure.

At Step 701, AD personnel, an automated computerized process, and/or any other type of computerized process may assign a unique Random User Device identifier (RUDD) to each user device for any number of users and provision such user devices as corresponding user endpoints in the AD (e.g., AD 100) to use the associated RUDD as its identifier when sending one or more received information tokens and/or information associated with the one or more received information tokens to a received token database (e.g., Received Token Database 504).

At Step 702, user endpoints periodically send received information tokens and/or information associated with the received information tokens (hereinafter simply "token reports") of the user device (e.g., together with the RUDID of the device and any associated information such as timestamps) to the Received Token Database 504. Since the incubation period of most diseases within the scope of this disclosure is typically long e.g., multiple days), the user endpoints may bundle token reports comprising data collected over any period of time (e.g., minutes of data, hours of data, days of data, weeks of data, etc.) and send such data to the Received Token Database 504 in batches. In various embodiments, the sending of the token reports from a given user endpoint is both periodic and ongoing. In some examples, user endpoints may send received token reports (e.g., directly from a user endpoint), in other examples, (e.g., based on example method 700) another element in the system acting as a proxy for the user endpoint (e.g., such element having equivalent token information and RUDID information) may send such information to the Received Token Database 504.

FIG. 7B is a flow diagram of an example method 750 for performing operations that support contact tracing based on acoustic communications while protecting user privacy, for example, after a person learns that they have tested positive for a disease. One or more portions of the example method 750 can be executed and/or implemented on one or more computing devices or computing systems. In addition, one or more portions of the example method 750 can be executed or implemented as an algorithm on the hardware devices or systems disclosed herein. FIG. 7B depicts steps performed in a particular order for purposes of illustration and discussion. As such, those skilled in the art, using the disclosures provided herein, will understand that various steps of any of the methods disclosed herein can be adapted, modified, rearranged, omitted, and/or expanded without deviating from the scope of the present disclosure.

At Step 751 "User B" learns that they have tested positive for a disease within the scope of this disclosure. At Step 752 "User B" notifies AD personnel or a contact tracing system associated with the AD of their positive test result, for example, by calling, by messaging, by email, and/or via direct interaction with a contact tracing application user interface provided via a computing device (e.g., provided via one of "User B's" User Devices). At Step 753 AD personnel, an automated computerized process, and/or any other type of computerized process may assemble a list of RUDIDs associated with all of User B's user devices and send this list of RUDIDs (e.g., only the specific list of RUDIDs) to a trusted received token database and correlation service that, for example, may execute the next two steps.

At Step 754 the trusted correlation service, using token reports associated with "User B's" user devices (e.g., those associated with one or more RUDIDs of Step 753), correlates those tokens with all other user devices to determine if an epidemiologically significant exposure between "User B" and one of those other users occurred via token reports in the Received Token Database 504. At Step 755, the trusted correlation service reports the RUDIDs of the user devices of potentially exposed individuals (e.g., or a null report or corresponding message indicating no RUDIDs of other users had exposure) back to the AD (e.g., AD 100). At Step 756, AD personnel, an automated computerized process, and/or any other type of computerized process) may perform a reverse lookup of the RUDIDs to determine the individual users that may have been exposed to "User B," notifies those users, and generates any required reports to appropriate authorities.

Figure 8:
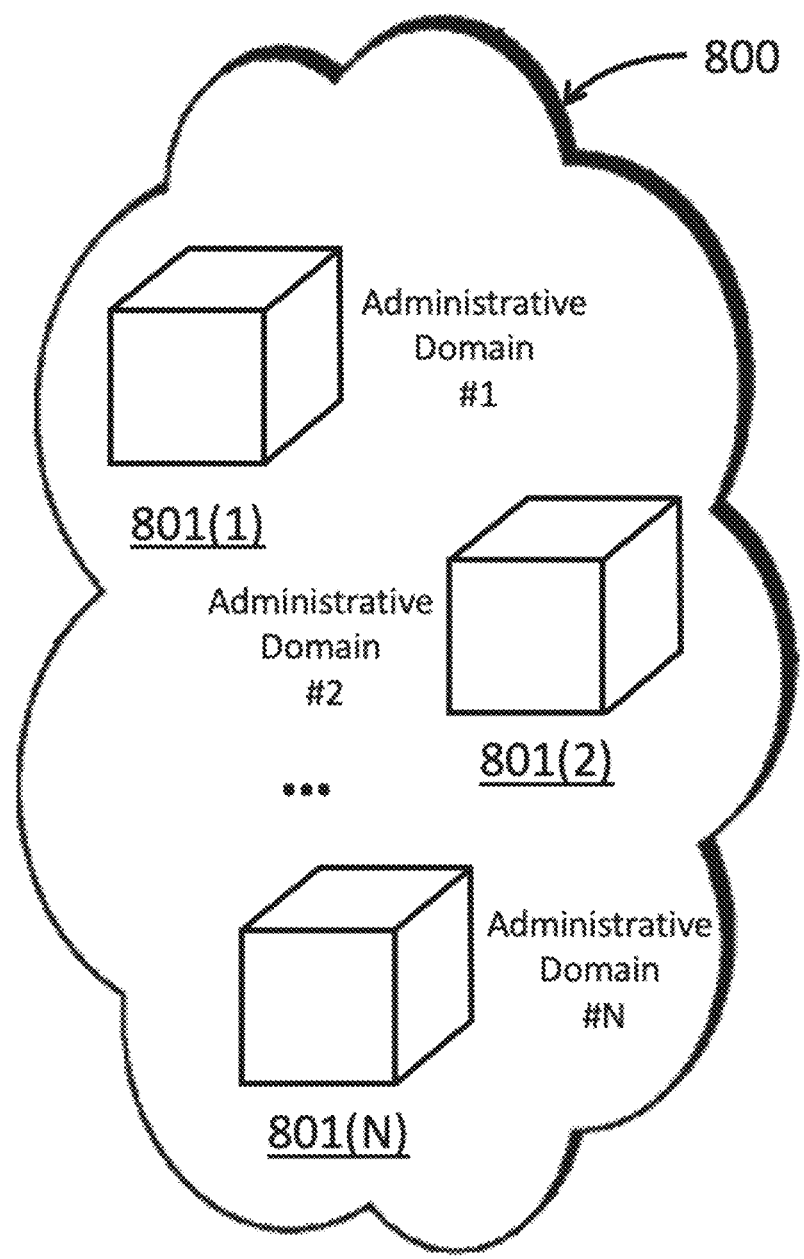
FIG. 8 is an illustration depicting an example of a federation of separate administrative domains, according to example embodiments of the present disclosure.

In an embodiment, if the privacy situation were such that the AV(s) where the exposure occurred need not be kept secret, the trusted correlation service could, for example in association with Step 755, report back the actual tokens along with the RUDIDs. As such, AD personnel could perform a reverse lookup of the actual Ad's via consultation with the sent token database (e.g., based on information in Sent Token Database 403). Persons skilled in the art will appreciate that some of the steps of example method 700 and/or example method 750 can be modified, added to, and/or occur in a different order to achieve the same or similar goals, FIG. 8 depicts an example of a federation of ADs. System 800, includes a federation of multiple ADs, labeled 801(1) through 801(N). In some embodiments, this configuration can exist, for example, when one or more ADs use compatible infrastructure (e.g., of the same manufacturer, compatible technology, etc.) and the entities controlling the respective ADs have a relationship by which using the token information in the relevant databases for each ND is consistent with their respective end-user permissions for sharing such information.

In an embodiment, information related to the received information tokens associated with a diseased person can be compared to information related to the received information tokens associated with other users in the same AD (e.g., same organization, same building, same campus, etc.) and/or in a federation of partnering ADs (e.g., another organization, another building of the same organization or a different organization, another campus of the same organization or a different organization, etc.).

Example Devices and Systems

Figure 9:
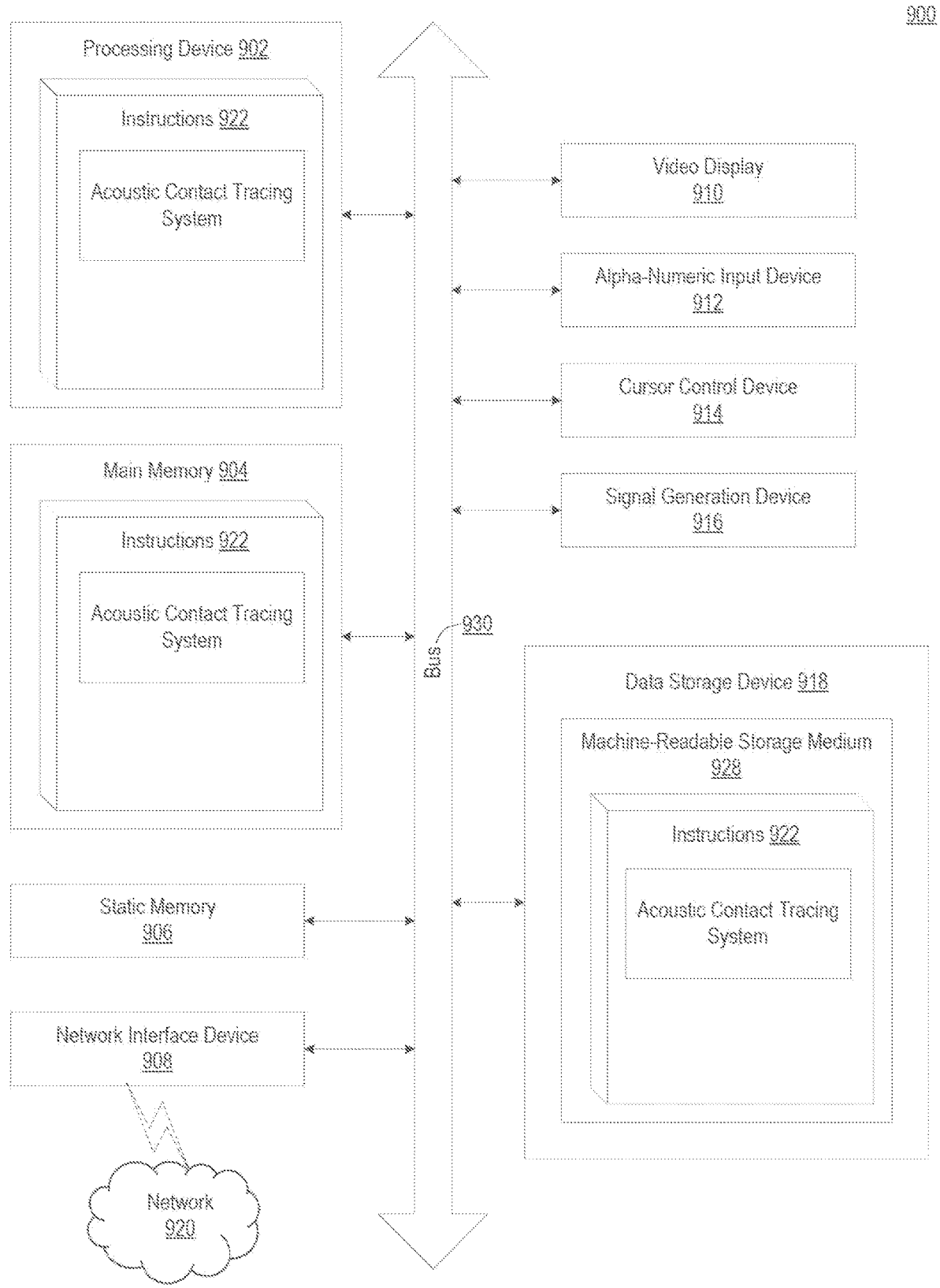
FIG. 9 depicts a block diagram of an example computer system that may perform one or more of the example embodiments of the present disclosure.

FIG. 9 illustrates a diagram of an example machine in the form of a computer system 900, within which a set of instructions for causing the machine to perform any one or more of the operations discussed herein may be executed. In other examples, the machine may be connected (e.g., networked) to other machines in a LAN, an intranet, an extranet, or the internet. The machine may operate in the capacity of a server or a client machine in a client-server network environment, or as a peer machine in a peer-to-peer (or distributed) network environment. The machine may be a personal computer (PC), a tablet PC, a set-top box (SIB), a Personal Digital Assistant (PDA), a cellular telephone, a wearable computing device, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the operations discussed herein.

Computer system 900 includes at least one processing device (e.g., processor 902), a main memory 904 (e.g., read-only memory (ROM), flash memory, dynamic random-access memory (DRAM) such as synchronous DRAM (SDRAM), double data rate (DDR SDRAM), or DRAM (RDRAM), etc.), a static memory 906 (e.g., flash memory, static random-access memory (SRAM), etc.), and a data storage device 918, which communicate with each other via a bus 930.

Processor 902 represents one or more processing devices such as a microprocessor, central processing unit, or the like. More particularly, the processor 902 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 902 also may be one or more special-purpose processing devices such as an application specific integrated circuit (ASIC), a field programmable gate array (FPGA), a digital signal processor (DSP), network processor, or the like. The processor 902 is configured to execute instructions 922 for performing the operations associated with an acoustic contract tracing system as discussed herein.

The computer system 900 also may include a network interface device 908. The computer system 900 may further include a video display unit 910 (e.g., a liquid crystal display (LCD), a plasma display, etc.), an alphanumeric input device 912 (e.g., a keyboard), a cursor control device 914 (e.g., a mouse), and a signal generation device 916 (e.g., a speaker).

The data storage device 918 may include a computer-readable storage medium 928 on which is stored one or more sets of instructions 922 (e.g., software computer instructions) embodying any one or more of the examples described herein. The instructions 922 also may reside, completely or at least partially, within the main memory 904 and/or within the processor 902 during execution thereof by the computer system 900, the main memory 904 and the processor 902 also constituting computer-readable storage media. The instructions 922 may be transmitted or received over a network 920 via the network interface device 908.

In one example, the instructions 922 include instructions for one or more modules of an acoustic contact tracing system in accordance with examples of the present disclosure and/or a software library containing methods that call an acoustic contact tracing system in accordance with examples of the present disclosure. While the computer-readable storage medium 928 (machine-readable storage medium) is shown as an example to be a single medium, the term "computer-readable storage medium" should be taken to include a single medium or multiple media (e.g., a centralized or distributed database, and/or associated caches and servers) that store the one or more sets of instructions. The term "computer-readable storage medium" also may include any medium that is capable of storing, encoding or carrying a set of instructions for execution by the machine and that cause the machine to perform any one or more of the operations of the present disclosure. The term "computer-readable storage medium" shall accordingly be taken to include, but not be limited to, solid-state memories, optical media, and magnetic media.

Numerous details are set forth in the foregoing description. However, it will be apparent to one skilled in the art having the benefit of this disclosure that the present disclosure may be practiced without these specific details. In some instances, well-known structures and devices are shown in block diagram form, rather than in detail, to avoid obscuring the present disclosure.

Some portions of the detailed description have been presented in terms of processes and symbolic representations of operations on data bits within a computer memory. Here, a process is generally conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "analyzing," "determining," "identifying," "adjusting," "transmitting," "receiving," "processing" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Certain examples of the present disclosure also relate to an apparatus for performing the operations herein. This apparatus may be constructed for the intended purposes, or it may comprise a computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

It is to be understood that the above description is intended to be illustrative, and not restrictive. Many other examples will be apparent to those of skill in the art upon reading and understanding the above description. The scope of the disclosure therefore should be determined with reference to the appended claims, along with the full scope of equivalents to which such claims are entitled.

Additional Disclosure

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one skilled in the art. For instance, features illustrated or described as part of one embodiment can be used with another embodiment to yield a still further embodiment. Thus, it is intended that the present disclosure cover such alterations, variations, and equivalents.

What is claimed is:

1. A computer-implemented method for performing contact tracing based on acoustic communications, comprising:
    obtaining, over a network and by one or more processor devices, information associated with one or more acoustic tokens from a first user device of a first user, the one or more acoustic tokens being associated with an emitter device that broadcasts acoustic tokens in an acoustic volume via an audio communication channel;
    obtaining, by one or more of the processor devices, information associated with one or more acoustic tokens from a second user device of a second user, the one or more acoustic tokens being associated with the emitter device;
    determining, by one or more of the processor devices, whether the second user was exposed to a disease associated with the first user in the acoustic volume based on analyzing the information associated with the one or more acoustic tokens from the first user device in view of the information associated with the one or more acoustic tokens from the second user device; and
    outputting, by one or more of the processor devices, information based on the determining of whether the second user was exposed to the disease associated with the first user in the acoustic volume.

2. The computer-implemented method of claim 1, wherein the outputting comprises:
    providing a notification to the second user indicating that the second user was exposed to the disease.

3. The computer-implemented method of claim 1, further comprising:
    providing the emitter device for broadcasting acoustic tokens in the acoustic volume.

4. The computer-implemented method of claim 3, wherein the emitter device is among a plurality of emitter devices of an administrative domain and each of the emitter devices broadcasts one or more acoustic tokens that each comprise a unique emitter device identification element associated with a corresponding one of the emitter devices.

5. The computer-implemented method of claim 1, wherein at least one of the first user device or the second user device performs decoding of the one or more acoustic tokens associated with the emitter device.

6. The computer-implemented method of claim 1, further comprising:
    receiving the information associated with the one or more acoustic tokens from the first user device; and
    storing the information associated with the one or more acoustic tokens received from the first user device in a database.

7. The computer-implemented method of claim 1, further comprising:
    receiving the information associated with the one or more acoustic tokens from the second user device; and
    storing the information associated with the one or more acoustic tokens received from the second user device in a database.

8. The computer-implemented method of claim 1, wherein each of the acoustic tokens associated with the emitter device comprises a static emitter identification element.

9. The computer-implemented method of claim 1, wherein each of the one or more acoustic associated with the emitter device comprise a static emitter identification element and a pseudorandom time element.

10. The computer-implemented method of claim 9, wherein the pseudo-random time element associated with each of the acoustic tokens is based on a corresponding result from a deterministic random word generator associated with the emitter device.

11. The computer-implemented method of claim 1, wherein each of the one or more acoustic tokens associated with the emitter device comprises an ephemeral emitter identification element.

12. The computer-implemented of claim 11, wherein verification of each ephemeral emitter identification element is performed for determining whether information associated with a corresponding acoustic token is trusted.

13. The computer-implemented method of claim 11, wherein the emitter device plays out one or more ordered sets of ephemeral emitter identification elements across a plurality of acoustic tokens broadcast in the acoustic volume.

14. The computer-implemented method of claim 13, wherein each of the ephemeral emitter identification elements in the one or more ordered sets of ephemeral emitter identification elements corresponds only to the emitter device in view of one or more other emitter devices in a same administrative domain as the emitter device.

15. The computer-implemented method of claim 1, further comprising:
    receiving information indicating that the first user tested positive for the disease.

16. The computer-implemented method of claim 1, wherein the information associated with the one or more acoustic tokens from the first user device is obtained based on a period of time associated with the disease.

17. The computer-implemented method of claim 1, wherein the information associated with the one or more acoustic tokens from the second user device is obtained based on a period of time associated with the disease.

18. The computer-implemented method of claim 1, wherein the determining that the first user was exposed to the disease is further based on information associated with radio frequency communication between the first user device and the second user device.

19. A computing system, comprising:
    one or more processors; and
    one or more non-transitory computer-readable media storing instructions that, when executed by the one or more processors, cause the one or more processors to:
    obtain, over a network, information associated with one or more acoustic tokens from a first user device of a first user, the one or more acoustic tokens being associated with an emitter device that broadcasts acoustic tokens in an acoustic volume via an audio communication channel;

obtain information associated with one or more acoustic tokens from a second user device of a second user, the one or more acoustic tokens being associated with the emitter device;

determine whether the second user was exposed to a disease associated with the first user in the acoustic volume based on analyzing the information associated with the one or more acoustic tokens from the first user device in view of the information associated with the one or more acoustic tokens from the second user device; and provide a notification to the second user indicating that the second user was exposed to the disease based at least in part on determining that the second user was exposed to the first user in the acoustic volume.

20. One or more tangible, non-transitory computer-readable media storing computer-readable instructions that, when executed by one or more processors, cause the one or more processors to:

obtain, over a network, information associated with one or more acoustic tokens from a first user device of a first user, the one or more acoustic tokens being associated with an emitter device that broadcasts acoustic tokens via an audio communication channel;

obtain information associated with one or more acoustic tokens from a second user device of a second user, the one or more acoustic tokens being associated with the emitter device;

determine whether the first user was exposed to a disease associated with the second user based on analyzing the information associated with the one or more acoustic tokens from the first user device in view of the information associated with the one or more acoustic tokens from the second user device; and output information based on determining whether the first user was exposed to the disease associated with the second user.

* * * * *